(12) United States Patent
Raghavan et al.

(10) Patent No.: US 9,002,499 B2
(45) Date of Patent: Apr. 7, 2015

(54) METHODS FOR DETERMINING A RECOVERY STATE OF A METAL ALLOY

(75) Inventors: Rajesh Raghavan, Bangalore (IN); Shashank Tiwari, Bangalore (IN); Sushil Kumar Mishra, Bangalore (IN)

(73) Assignee: GM Global Technology Operations LLC, Detroit, MI (US)

( * ) Notice: Subject to any disclaimer, the term of this patent is extended or adjusted under 35 U.S.C. 154(b) by 417 days.

(21) Appl. No.: 13/425,356

(22) Filed: Mar. 20, 2012

(65) Prior Publication Data

US 2013/0253691 A1    Sep. 26, 2013

(51) Int. Cl.
G06F 19/00 (2011.01)
G01N 23/203 (2006.01)

(52) U.S. Cl.
CPC ........ G01N 23/203 (2013.01); *G01N 2223/606* (2013.01); *G01N 2223/615* (2013.01)

(58) Field of Classification Search
USPC ............................ 700/145; 148/554; 420/471
See application file for complete search history.

(56) References Cited

U.S. PATENT DOCUMENTS

| | | | |
|---|---|---|---|
| 2008/0289958 A1* | 11/2008 | Kardokus et al. | 204/298.12 |
| 2009/0020192 A1* | 1/2009 | Segal et al. | 148/536 |
| 2011/0192505 A1* | 8/2011 | Kaneko et al. | 148/554 |
| 2011/0223056 A1* | 9/2011 | Aruga et al. | 420/471 |

OTHER PUBLICATIONS

Kamaya, Masayuki, et al., "Measurement of plastic strain of polycrystalline material by electron backscatter diffraction", Science Direct, Nuclear Engineering and Design 235, (2005), pp. 713-725.

Verdier, M., et al., "Recovery of AlMg Alloys: Flow Stress and Strain-Hardening Properties", Acta mater. vol. 47, No. 1, (1999), pp. 127-134.

Chihab, K., et al., "The Kinetics of the Portevin-Le Chatelier Bands in an A1-5at%Mg Alloy", Scripta Metallurgica, vol. 21, (1987), pp. 203-208.

Verdier, M., et al., "Dislocation Densities and Stored Energy After Cold Rolling of Al-Mg Alloys: Investigations by Resistivity and Differential Scanning Calorimetry", Scripta Materialia, vol. 37, No. 4, (1997), pp. 449-454.

Shercliff, H. R., et al., "A Process Model for Age Hardening of Aluminium Alloys—I. The Model", Acta metal. mater. vol. 38, No. 10, (1990), pp. 1789-1802.

Cho, Jae-Hyung, et al., "Investigation of Recrystallization and Grain Growth of Copper and Gold Bonding Wires", Metallurgical and Materials Transactions A, vol. 37A, Oct. 2006, pp. 3085-3097.

Wright, Stuart I., et al., "EBSD Image Quality Mapping", Microscopy Microanalysis 12, (2006), pp. 72-84.

(Continued)

*Primary Examiner* — Robert Fennema
*Assistant Examiner* — Anthony Whittington
(74) *Attorney, Agent, or Firm* — Dierker & Associates, P.C.

(57) ABSTRACT

Methods for determining a recovery state of a metal alloy are disclosed herein. In one example, a fluctuation in a crystallographic grain orientation of the metal alloy is determined by utilizing electron backscatter diffraction (EBSD) data of the metal alloy. A processor of an electron backscatter diffraction machine utilizes a local orientation deviation quantifier to correlate the fluctuation in the crystallographic grain orientation of the metal alloy with a plastic strain recovery of the metal alloy. Other examples of the method are also disclosed herein.

16 Claims, 4 Drawing Sheets
(2 of 4 Drawing Sheet(s) Filed in Color)

(56) References Cited

OTHER PUBLICATIONS

Lee, Theresa M., et al., "Demonstration of the Preform Anneal Process to Form a One-Piece Aluminum Door Inner Panes", SAE Technical Paper Series 2006-01-0987, (2006), 9 pages.
Diak, B. J., et al., "Recovery of Tensile Properties of AA5182 after Cold Rolling", Materials Science Forum vols. 519-521, (2006), pp. 1653-1658.
Stuwe, H.P., et al., "Competition between recovery and recrystallization", Materials Science and Engineering A333, (2002), 361-367.
Sarkar, S., et al., "Softening behaviour of cold rolled continuous cast and ingot cast aluminum alloy AA5754", Materials Science and Engineering A 421, (2006), pp. 276-285.
Peranio, N., et al., "Microstructure and texture evolution in dual-phase steels: Competition between recovery, recrystallization, and phase transformation", Materials Science and Engineering A 527, (2010), pp. 4161-4168.
Pantleon, W., "Resolving the geometrically necessary dislocation content by conventional electron backscattering diffraction", Scripta Materialia 58, (2008), pp. 994-997.
Oyarzabal, Maite, et al., "Sensitivity of Conventional and Non-destructive Characterization Techniques to Recovery and Recrystallization" ISIJ International, vol. 47, No. 10, (2007), pp. 1458-1464.
Michalak, J.T., et al., "Some Recovery Characteristics of Zone-Melted Iron", Transactions of the Metallurgical Society of AIME, vol. 221, Aug. 1961, pp. 850-857.
Liu, W.C., et al., "Evolution of Recrystallization and Recrystallization Texture in Continuous-Cast AA 3015 Aluminum Alloy", Metallurgical and Materials Transactions A, vol. 36A, Oct. 2005, pp. 2829-2848.
Li, Jingjing, et al., "The effect of prestrain and subsequent annealing on the mechanical behavior of AA5182-O", Materials Science and Engineering A 528, (2011), pp. 3905-3914.
Hurley, P.J., et al., "The application of EBSD to the study of substructural development in a cold rolled single-phase aluminium alloy", Science Direct, Acta Materialia 51, (2003), 1087-1102.
Field, David P., "Quantification of partially recrystallized polycrystals using electron backscatter diffraction", Materials Science and Engineering A190, (1995), pp. 241-246.
El-Dasher, B.S., et al., "Viewpoint: experimental recovery of geometrically necessary dislocation density in polycrystals" Scripta Materialia 48, (2003), pp. 141-145.
Dzubinsky, M., et al., "Comparison of recrystallisation kinetics determined by stress relaxation, double hit, optical metallography and EBSD approaches", Materials Characterization 52, (2004), pp. 93-102.
Demir, Eralp, et al., "Investigation of the indentation size effect through the measurement of the geometrically necessary dislocations beneath small indents of different depths using EBSD tomography", ScienceDirect, Acta Materialia 57, (2009), pp. 559-569.
Dziaszyk, S., et al., "On the characterization of recrystallized fraction using electron backscatter diffraction: A direct comparison to local hardness in an IF steel using nanoindentation", Materials Science and Engineering A 527, (2010), pp. 7854-7864.
Yao, Z., et al., "Application of EBSD in Deformation Microstructure Characterization", Journal of Chinese Electron Microscopy Science, vol. 27, No. 6, 2008, pp. 452-456.
Li, X., et al., "EBSD Analyses on Recovery and Recrystailization of High Purity Cold Rolled Nickel", Chin. J. of Stereology and Mage Analysis, vol. 10, No. 4, Dec. 2005, pp. 221-210.

* cited by examiner

US 9,002,499 B2

METHODS FOR DETERMINING A RECOVERY STATE OF A METAL ALLOY

TECHNICAL FIELD

The present disclosure relates generally to methods for determining a recovery state of a metal alloy.

BACKGROUND

Some metal forming processes utilize a stamping or other similar operation to form a sheet metal panel into a desired shape. Several metal forming processes are available. One example of a metal forming process includes a pre-forming step, followed by a thermal treatment step, and then a final forming step. The formed sheet metal panel may then be used as a part, such as, e.g., an automotive body part.

SUMMARY

Methods for determining a recovery state of a metal alloy are disclosed herein. One example includes determining a fluctuation in a crystallographic grain orientation of the metal alloy by utilizing electron backscatter diffraction (EBSD) data of the metal alloy. A local orientation deviation quantifier is then used by a processor of an electron backscatter diffraction machine to correlate the fluctuation in the crystallographic grain orientation of the metal alloy with a plastic strain recovery of the metal alloy.

Other examples of methods for determining a recovery state of a metal alloy are also disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Plastic deformation of a metal alloy may occur when the metal is formed into a desired shape. Deformation may induce dislocation flux that causes crystallographic orientation changes or fluctuations in localized regions within individual grains of the metal alloy. It is believed that the crystallographic orientation changes or fluctuations occur in order to accommodate gradients formed in the grains during the process used to form/shape the metal. Further, the crystallographic orientation changes within a grain are related to a stored dislocation density, and thus the orientation changes may be utilized as indicators of stored work in the metal alloy. With deformation of the metal alloy, stored work may not be uniform over an entire grain. Information pertaining to the orientation changes within the grains may be useful for determining the mechanical behavior (e.g., the formability) of the metal alloy.

It has been found that the metal forming process may be controlled based, at least in part, on the recovery and recrystallization characteristics of the metal alloy. For instance, total elongation of the alloy may be extended and formability of the alloy may be enhanced during the metal forming process based, at least in part, on the recovery characteristic of the metal alloy. The recovery of stored work in the metal alloy may be said to be equivalent to resetting the plastic state of the alloy back to its initial state without changing the morphology of the alloy. As such, large plastic strains of the alloy may be achieved with intermittent heat treatments. For example, the extended total elongation and enhanced formability may be obtained by adding thermal treatment step(s) (e.g., annealing) to the metal forming process (e.g., between stamping operations). However, recovery may compete with recrystallization. As such, in some instances, complete recovery of stored energy of the metal alloy may not be possible when the stored energy is instead consumed through recrystallization of the alloy.

The inventors of the present disclosure have found it both useful and beneficial to determine or track the recovery state of the metal alloy, and to recognize the onset of recrystallization. This information may be used, e.g., to design a forming process specific for that metal alloy. The recovery state of the metal alloy and the onset of recrystallization may be determined using the example methods disclosed herein. Each of these methods utilizes electron backscatter diffraction (EBSD) data, and by visual observation, one or more fluctuations in a crystallographic grain orientation of the metal alloy may be determined. It has been found that a reduction in dislocation density that leads to recovery of the metal alloy can be identified by an observed decay of grain orientation fluctuations. The observed orientation fluctuation(s) (as opposed to the mean orientation) may then be correlated with the plastic strain recovery of the metal alloy.

Figure 1:
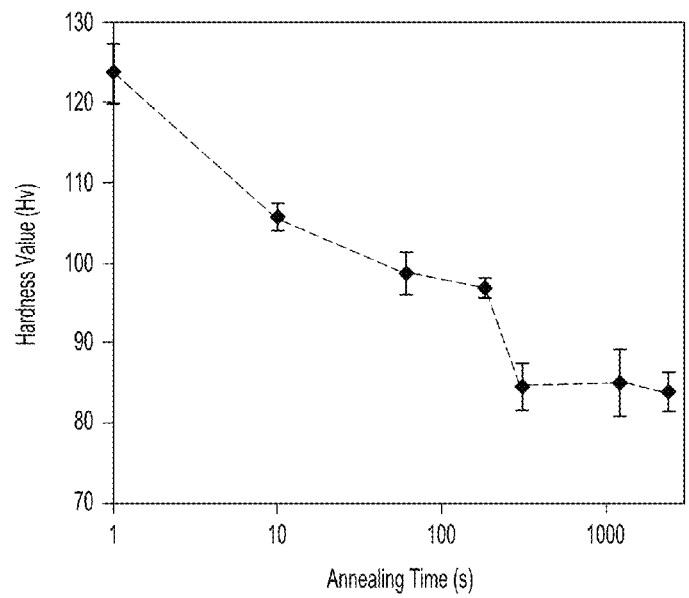
FIG. 1 is a plot showing the relationship between the Vickers Hardness value for an AA5182 aluminum alloy and annealing time.

By the methods disclosed herein, the recovery state of the metal alloy may be determined directly, and with better accuracy compared to other methods. In an example, other methods that track recovery may produce data lacking a decipherable trend, and the recovery state of the metal alloy may not be readably determinable. In another example of these other methods, the onset of recrystallization of the metal alloy sample may be determined by measuring the Vickers hardness value (Hv) of the metal alloy sample as the sample is annealed over time (seconds). A plot of the Vickers hardness value of a metal alloy versus annealing time is shown in FIG. 1. The Vickers hardness value for the plot was measured using a CSM microhardness tester (CSM Instruments, Needham Heights, Mass.) with a Vickers diamond indenter. The plot in FIG. 1 shows a recovery of the metal alloy by the gradual reduction in hardness as annealing continues up to about 180 seconds. At this time, the hardness of the metal alloy drops suddenly. It is believed that this drop in hardness (which is a sudden softening of the metal alloy) is indicative of the onset of recrystallization of the metal alloy. While not evident from the indirect hardness measurements, it is further believed that the onset of recrystallization may have occurred before 180 seconds.

The example methods disclosed herein may be used to determine the recovery state of any metal alloy. These methods are particularly useful for determining the recovery state of precipitation-hardenable (which includes age-hardenable) metal alloys. Generally, the recovery of a deformed metal alloy is due to dislocation-dislocation interactions and dislocation densities of the alloy. One way to measure the recovery is to measure the softening of the alloy using a hardness tester as previously described. For non-precipitation hardenable alloys, the hardness of the alloy is based, at least in part, on dislocation-dislocation interactions, and thus, a loss in hardness may be correlated to changes in those dislocation-dislocation interactions. For precipitation-hardenable alloys, hardness is based, at least in part, on dislocation-precipitate interactions. Precipitate morphology and distribution change during annealing, which changes dislocation-precipitate interactions. Hardness testing of these alloys does not reveal changes in dislocation-dislocation interactions, and thus does not identify recovery.

The method according to the examples disclosed herein does not rely on dislocation-precipitate interactions, and may be used to determine the recovery of the alloy without having to rely on hardness testing. The method(s) disclosed herein focus on grain orientation fluctuations (which are observable from the IPF maps described in further detail below), and these orientation fluctuations are related to changes in groups of dislocations and grain substructures. In this way, the method may be used to directly determine the recovery of precipitation-hardenable metal alloys.

Some examples of precipitation-hardenable metal alloys for which the examples of the method may be used to determine recovery include aluminum alloys (such as, e.g., Al—Mg—Si—Cu alloys, Al—Cu alloys, and Al—Zn alloys), copper alloys (such as, e.g., Be—Cu alloys, Zr—Cu alloys, Cu—Ni—P alloys, and Cu—Ni—Si alloys), and magnesium alloys (such as, e.g., Mg—Sn alloys, Mg—Sm alloys, and Mg—Nd alloys).

Further, the metal alloy may be formed into a part having a desired shape, and this may be accomplished using a metal forming process. In an example, the metal forming process includes a thermo-mechanical treatment step, an example of which is an annealing step. The annealing step may be performed between stamping operations. The formed part may be used as an automotive part, such as a body panel or structural part, and may be made using an automotive forming process. The part may otherwise be used for other applications, such as for airplanes, boats, buildings, construction, etc.

In one example method, a fluctuation in the crystallographic grain orientation of the metal alloy is determined utilizing EBSD data of the metal alloy. The EBSD data may be obtained from an EBSD machine that is designed to determine the crystallographic grain orientation of a sample, which in this case is the metal alloy. The EBSD machine is further designed to index and identify the crystallography of the sample (e.g., the crystal lattice system including space groups, lattices, crystals, and the like). The crystallography information may then be used for crystal orientation mapping, for determining crystal defects, for phase identification, for determining grain boundary and morphology, etc. In an example, the ESBD machine is a scanning electron microscope (SEM) equipped with an EBSD detector that contains at least a phosphor screen, a compact lens, and a low light charge-coupled (CCD) camera chip having any resolution as desired. In an example, the CCD camera is selected to have a resolution of up to about 1600×1200 pixels.

The EBSD data may be obtained by putting the sample metal alloy in the SEM chamber at an appropriate angle so that the sample faces the CCD camera. The phosphor screen is located within the SEM chamber and is coupled to the compact lens that focuses an image of the metal alloy sample from the phosphor screen onto the CCD camera. Electrons backscatter within the metal alloy sample, and as the backscattering electrons exit the sample, they exit at an angle indicative of the spacing of the periodic atomic lattice planes of the metal alloy sample. The exit angle is known as the Bragg angle. The electrons can then escape the metal alloy, and in doing so, some of the electrons may collide and exit the phosphor causing it to fluoresce.

The EBSD machine may also be used to find the crystal orientation of the metal alloy, and this may be accomplished by scanning an electron beam of the machine in a predefined fashion (e.g., by a square or hexagonal grid). The results of the scan may be used to describe the crystallographic grain orientation, microtexture, and morphology of the metal alloy sample. EBSD data may then be used to generate a graph that plots, for example, the relationship between the area or number fraction of the metal alloy sample and a local average orientation deviation corresponding to one of a plurality of ESBD scan points.

Inverse pole figure (IPF) maps may be produced from some of the EBSD data. Examples of IPF maps are shown in FIGS. 2A through 2E, and these maps show the fluctuations in crystallographic grain orientations of the metal alloy sample. The maps shown in FIGS. 2A through 2E were produced using an AA5182 aluminum alloy sample (an aluminum alloy containing factions of Mg, Mn, Fe, Si, Cu, Ni, Ti, and Zn) deformed by a stamping operation of a metal forming process. The aluminum alloy sample was prepared by mechanical polishing using a diamond paste suspension, followed by electropolishing using an A2 electrolyte at 15V for 30 seconds. Large areas of the aluminum alloy sample were scanned with a spatial scan step of about 0.5 μm, and smaller areas of the sample were rescanned with a spatial scan step of about 0.1 μm to examine finer grain structures of the sample.

Figure 2A:
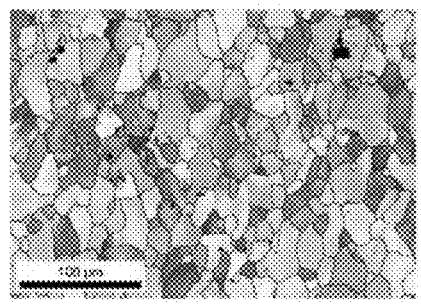
FIGS. 2A through 2E are electron backscatter diffraction (EBSD) inverse pole figure (IPF) maps of a 15% deformed AA5182 aluminum alloy exposed to no annealing step (FIG. 2A), 10 seconds of annealing (FIG. 2B), 60 seconds of annealing (FIG. 2C), 180 seconds of annealing (FIG. 2D), and 300 seconds of annealing (FIG. 2E)
Figure 2B:
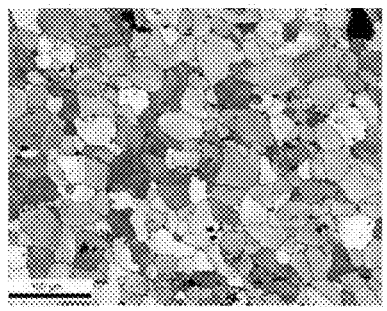
Figure 2C:
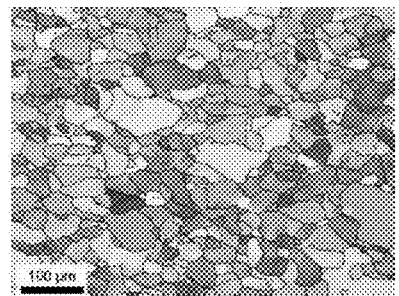
Figure 2D:
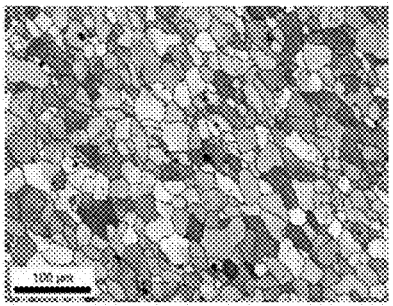
Figure 2E:
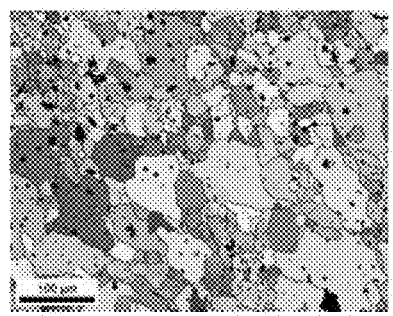
Figure 2F:
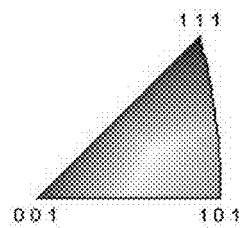
FIG. 2F is a color code for the IPF maps of FIGS. 2A through 2E.

FIG. 2A is an IPF map of the sample that was not exposed to annealing, while FIGS. 2B through 2E are IPF maps of other samples that were isothermally annealed for varying times at 350° C. FIG. 2F illustrates the color code of the grain orientation of a sample plane normal at an EBSD scan point of the metal alloy sample. Variations of color within a single grain of the metal alloy reflect fluctuations of grain orientation, and these fluctuations correspond to stored work in the metal alloy. As previously mentioned, a decay in a fluctuation of the grain orientation may indicate a reduction in dislocation density, and thus a reduction in stored work leading to recovery. In an example, the fluctuation(s) in grain orientation are determined by visually observing the variation(s) in color (i.e., color changes) within a single grain utilizing the color key of FIG. 2F. For instance, the grain $G_1$ shown in FIG. 2B has a variation in color between pink, blue, and white, and this may indicate fluctuation(s) in the sample plane normal orientation of somewhere between a (001) orientation and a (111) orientation. The grain $G_2$ also shown in FIG. 2B has a variation in the colors green and yellow, and this may indicate fluctuation(s) in the sample plane normal orientation of somewhere between a (001) orientation and a (101) orientation.

The fluctuation(s) in the crystallographic grain orientation may then be used to determine the recovery state of the metal alloy. It has been found that recovery of the metal alloy occurs during the thermal treatment step(s) (e.g., annealing) of the metal forming process. After being exposed to annealing at high temperatures (e.g., at or above 350° C. for the AA5182 aluminum alloy sample) for a certain time, the metal alloy may transition from a fully recovered state to a recrystallized state. As shown in the IPF maps of FIGS. 2B and 2C, some progressive recovery of the metal alloy sample was visually observable between 10 seconds and 60 seconds of annealing time. Visual observation of the IPF map of FIG. 2D showed that non-homogenous recrystallization and grain growth of the metal alloy occurs after about 180 seconds of annealing. Full recrystallization of the metal alloy was evident (by visual inspection of the IPF map of FIG. 2E) after 300 seconds of annealing, where the individual grains no longer exhibited a variation in color. This recrystallization was dominated by grain coarsening.

The inventors of the present disclosure have found that the transition point between the recovery state of the metal alloy and the onset of the recrystallization state (e.g., as shown between the IPF maps of FIGS. 2C and 2D) may be accurately identified by quantifying the recovery of the metal alloy. In an example, the recovery may be quantified utilizing a local orientation deviation quantifier to correlate the fluctuation(s) in the crystallographic grain orientation with a plastic strain recovery of the metal alloy. The local orientation deviation quantifier is determined by evaluating a local average orientation deviation (in degrees) at each EBSD scan point of the metal alloy from a respective reference orientation at each of the EBSD scan points. The evaluation of the local average orientation deviation is accomplished by a processor of the EBSD machine or a processor operatively connected to the EBSD machine that receives and analyzes the EBSD raw data. This processor may be incorporated into the EBSD machine (e.g., as a microprocessor, a processing chip, or the like), or may be part of a computing device that is separate from, but operatively connected to the EBSD machine. The computing device may be a personal computer, laptop, or the like, and may be wirelessly connected to the EBSD machine or connected to the EBSD machine via a wire. Further, the processor of the EBSD machine is configured to run computer programs containing computer readable code or instructions for performing the evaluation, wherein the code/instructions are embedded on a tangible, non-transitory computer readable medium. The processor may further run other computer readable code for performing other steps of the example methods disclosed herein, and these steps will be described in detail below. In an example, the processor runs EBSD analysis software to evaluate the local average orientation deviation. For the examples provided herein, the software used was EDAX OIM® analysis software (Version 5.0) commercially available from EDAX® Inc., Mahwah, N.J.

In an example, the local average orientation deviation is evaluated by calculating, by the processor running computer readable code, a difference between a measured orientation and the reference orientation. In other words, the local average orientation deviation is calculated as a mean of deviation of the orientation at a point (i.e., the measured orientation) that is located within a specified distance from the reference orientation at a reference point. The measured orientation is extracted from EBSD data produced by the EBSD machine upon testing a sample of the metal alloy. Since the calculation of the local average orientation deviation is based upon a distance from a reference point, the method disclosed herein is not dependent upon the EBSD scan parameters. The reference orientation may, in one example, be obtained as a mean kernel orientation (or kernel mean orientation). As used herein, a "kernel" refers to a set of points of a prescribed size surrounding the EBSD scan point of interest, and the size of the kernel is prescribed to the nth nearest neighbor. Second ($2^{nd}$) order neighbors correspond to the size of the kernel in order to calculate the mean orientation, where the term "$2^{nd}$ order" refers to the nearest and next-nearest neighbors being taken into account for the purposes of local deviation and mean orientation calculations. The "mean kernel orientation" refers to the average orientation of a point and all of its neighbors within the kernel, and may be referred to as a local orientation spread in analysis computer readable code run by the processor. This characterizes orientation fluctuation in the neighborhood of a point on the map. In other examples, the reference orientation may be a mean grain orientation or a grain orientation at a user-specified point inside a grain. As mentioned above, with deformation, the stored work may not be uniform over an entire grain. The gradual change of orientation within a grain may be accounted for in the local orientation deviation quantifier through the reference orientation that varies within the grain.

The local average orientation deviation may be calculated at each scan point, and thus in some instances, the data set for determining recovery states may be large. The data produced provides low noise distribution curves, even for small scan areas. It is to be understood that small scan areas are generally sufficient to identify the recovery and recrystallization as described herein. In an example, the scan area for the recovery determination of the AA5182 aluminum alloy used 400×250 micrometer-square area scans. It is to be understood, however, that 100×100 micrometer-square area scans (which may contain about 20 grains) may be sufficient to accurately obtain the peak orientation deviation angles described below.

Figure 3:
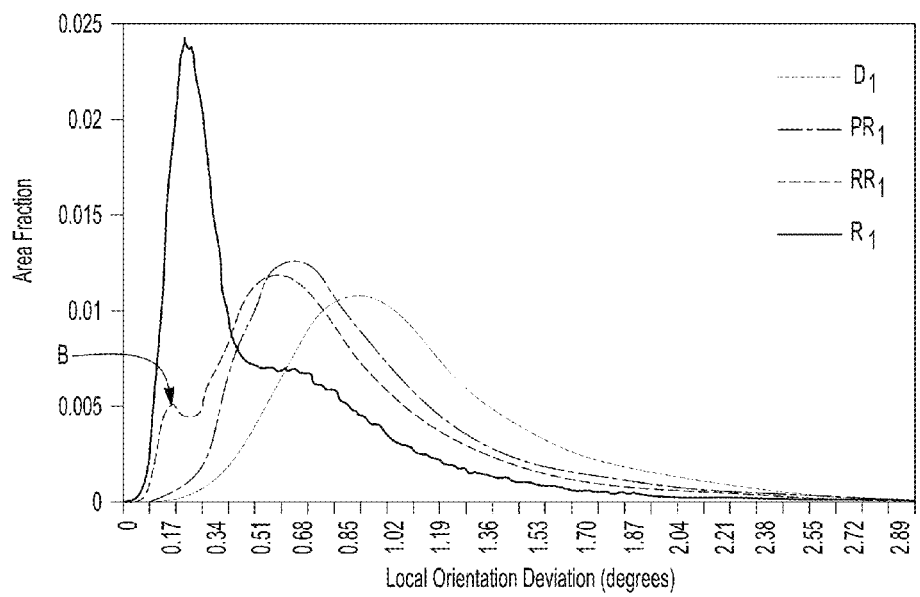
FIG. 3 is a plot showing distribution curves ($D_1$, $PR_1$, $RR_1$, and $R_1$) showing recovery and recrystallization of the AA5182 aluminum alloy sample during annealing.

After the local average orientation deviation of each scan point is calculated, the processor, running suitable computer readable code, plots an area fraction of the local average orientation deviation at each of the EBSD scan points. One example of this plot is shown in FIG. 3. This plot was produced utilizing the EBSD data for the AA5182 aluminum alloy, again which is a precipitation-hardenable metal alloy. Further, this plot includes several curves, where one of these curves represents the metal alloy in a deformed state (labeled with the reference character $D_1$), another curve represents the metal alloy in a partially recovered state (labeled with the reference character $PR_1$), yet another curve represents the metal alloy in a partially recovered state and at the onset of recrystallization (labeled with the reference character $RR_1$), and a curve that represents the metal alloy in a fully recrystallized state (labeled with the reference character $R_1$).

As shown in FIG. 3, the curve $D_1$ was produced after 15% pre-forming has occurred and after zero seconds of annealing time (i.e., the partially-deformed metal alloy was not subjected to annealing). Since no heat is added to the system, the curve $D_1$ represents the metal alloy in the fully deformed state after the initial stamping operation of the forming process. The curve $PR_1$ was produced after about 60 seconds of annealing time (where annealing was performed at 350° C.), and the introduction of the heat by the annealing step initiates recovery of the metal alloy sample. After further annealing (e.g., 180 seconds of annealing at 350° C.), the curve $RR_1$ was produced for the metal alloy sample that is yet further recovered (i.e., there is a decreased area fraction of recovery). The metal alloy is fully recovered (i.e., has obtained its maximum recovery) at this point. As used herein, "full recovery" or "complete recovery" of the metal alloy refers to the maximum possible recovery of the metal alloy prior to recrystallization. It is to be understood that the maximum possible recovery of the metal alloy prior to recrystallization, in some instances, may not be the complete resetting of the metal alloy back into its initial, non-deformed state. For instance, the maximum possible recovery of the metal alloy may be 95%, which is shy of completely resetting the metal alloy back into its initial state. However, in this instance, the maximum possible recovery of 95% is considered to be full or complete recovery.

As shown in FIG. 3, when the metal alloy sample is dominated by recovery kinetics, one broad peak above about 0.5 degrees is present (e.g., curve $PR_1$).

The onset of recrystallization is evident in curve $RR_1$ by the additional peak or blip B in the curve (i.e., an increased area fraction of recrystallization), which for this sample, occurs at about 0.2 degrees (i.e., the angle at the additional peak on curve $RR_1$). In FIG. 3, the curve $R_1$ represents full recrystallization of the metal alloy sample, and this occurred after about 300 seconds of annealing time at 350° C. The full recrystallization of this metal alloy sample is shown at about 0.3 degrees (i.e., the angle at the peak on curve $R_1$). The bimodal nature of both of the curves $RR_1$ and $R_1$ illustrates the decreasing area fraction of recovery and the increasing area fraction of recrystallization. The integrated area for the lowest local orientation deviation peaks corresponds to the area of recrystallization. It is believed that these statistics are robust enough to provide a distinct signature for a small recrystallization area fraction.

Figure 4:
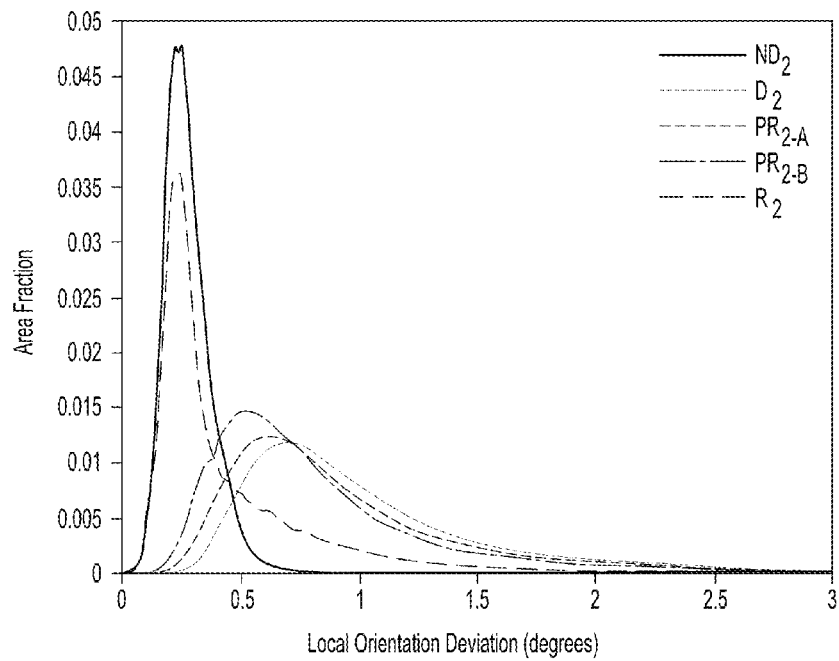
FIG. 4 is a plot showing distribution curves ($ND_2$, $D_2$, $PR_{2-A}$, $PR_{2-B}$, and $R_2$) showing recovery and recrystallization of an age-hardenable metal alloy sample during annealing.

An example of a plot of the area fraction of the local average orientation deviation at each EBSD scan point of another metal alloy is shown in FIG. 4. For this plot, EBSD data was obtained (by the EBSD machine) for an age-hardenable metal alloy; specifically an Al—Mg—Si—Cu alloy containing fractions of Fe, Mn, Cr, Ti, and Zn. The local average orientation deviation was calculated in the same manner as described above for the AA5182 aluminum alloy. FIG. 4 includes several curves, where one of these curves represents the metal alloy in a deformed state (labeled with the reference character $D_2$), another curve represents the metal alloy in a partially recovered state (labeled with the reference character $PR_{2-A}$), yet another curve represents the metal alloy in a partially recovered state (labeled with the reference character $PR_{2-B}$), and still another curve represents the metal alloy in a fully recrystallized state (labeled with the reference character $R_2$). FIG. 4 also includes another curve, which represents the metal alloy prior to pre-deformation, and this curve is labeled with the reference character $ND_2$.

As shown in FIG. 4, the curve $D_2$ was produced after 15% pre-forming has occurred and after zero seconds of annealing time (i.e., the partially-deformed metal alloy was not subjected to annealing). Since no heat is added to the system, the curve $D_2$ represents the age-hardenable metal alloy sample in the fully deformed state after the initial stamping operation of the forming process. The curve $PR_{2-A}$ was produced after about 60 seconds of annealing time (where annealing was performed at 410° C.), and the introduction of the heat by the annealing step initiates recovery of the metal alloy sample. After further annealing (e.g., 180 seconds of annealing at 410° C.), the curve $PR_{2-B}$ was produced for the metal alloy sample that is yet further recovered (i.e., there is a decrease in the peak orientation deviation angle). As shown in FIG. 4, when the metal alloy sample is dominated by recovery kinetics, one broad peak above about 0.5 degrees is present (e.g., curve $PR_{2-A}$).

In FIG. 4, the curve $R_2$ represents full recrystallization of the age-hardenable metal alloy sample, and this occurred after about 20 minutes of annealing time still at 410° C. Data corresponding to the onset of recrystallization was not obtained for the age-hardenable metal alloy; however it is known that the onset of recrystallization of the age-hardenable metal alloy is at about the 5 minute mark. The full recrystallization of this metal alloy sample is shown at about 0.3 degrees (i.e., the angle at the peak on curve $R_2$). The curve $R_2$, indicative of full recrystallization, has a single peak and no recovery information.

After the local average orientation deviation has been evaluated as described above, the processor running suitable computer readable code identifies a local orientation deviation angle θ at each of the EBSD scan points. For purposes of illustration, the local orientation deviation angle θ was identified for each of the peaks of the curves $D_1$, $PR_1$, $RR_1$, $R_1$ (shown in FIG. 3) produced from the raw EBSD data for the AA5182 aluminum alloy (i.e., precipitation-hardenable metal alloy) sample that was tested. It is to be understood that the identification of the local orientation deviation angle θ and ultimately quantification of the recovery may also be performed using the data produced from the plot shown in FIG. 4 for the age-hardenable metal alloy sample.

Figure 5A:
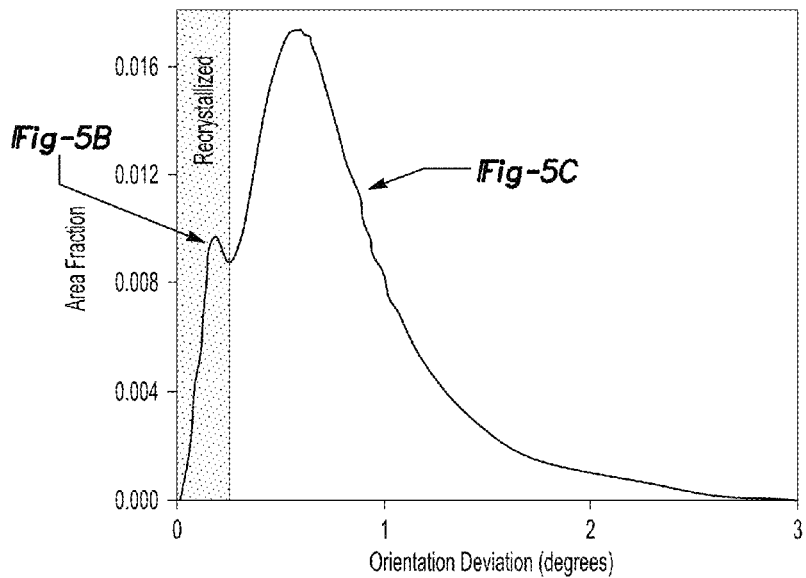
FIG. 5A is a plot showing the distribution curve $R_1$ of FIG. 3.
Figure 5B:
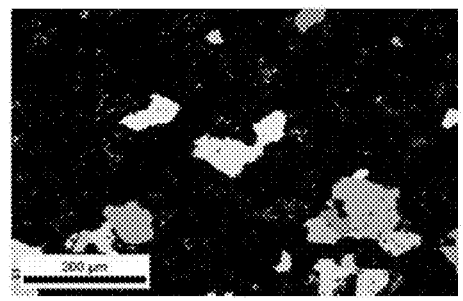
FIG. 5B is an IPF map of the entire AA5182 aluminum alloy sample annealed at 350° C. for 180 seconds.
Figure 5C:
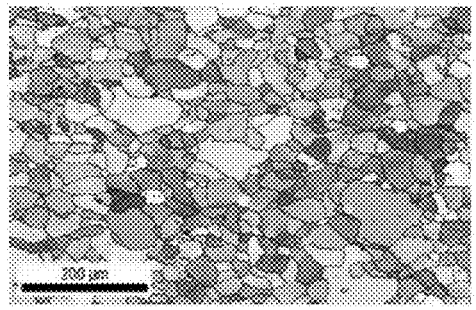
FIG. 5C is an IPF map of a segmented recrystallized portion of the AA5182 aluminum alloy sample annealed at 350° C. for 180 seconds.

In an example, the processor identifies $θ_{reference}$, a peak local orientation deviation angle for the AA5182 aluminum alloy in the deformed state. This is shown by the peak of the curve $D_1$ in FIG. 3. The processor also identifies $θ_{recovery}$, a peak local orientation deviation angle for the metal alloy in an at least partially recovered state. $θ_{recovery}$ is shown by the peak of the curve $PR_1$ in FIG. 3. It has been found that at least partial recovery of the metal alloy occurs when $θ_{recovery}$ is less than $θ_{reference}$. The processor further identifies $θ_{recrystallization}$, a peak local orientation deviation angle for the metal alloy when it is fully recrystallized. $θ_{recrystallization}$ is shown by the peak of the curve $R_1$ in FIG. 3. As previously mentioned, at the onset of recrystallization, the metal alloy is partially recovered and partially recrystallized. In this instance, the curve $RR_1$ in FIG. 3 will have two peaks; one representing the local orientation deviation angle for partial recovery of the metal alloy, and the other representing the local orientation deviation angle for partial recrystallization of the metal alloy. FIG. 5A is a reproduction of the curve $RR_1$ from FIG. 3, where the peak for recovery and the peak for recrystallization are clearly shown. FIG. 5B is an IPF map showing the entire metal alloy sample tested, which includes the recovery portion of the metal alloy. FIG. 5C is another IPF map showing the segmented recrystallized portion of the metal alloy. The segmentation corresponds to the scan points in the sample with location orientation deviation less than 0.3 degrees. As shown in these maps, recrystallized grains have been captured with relatively good accuracy, at least in part because the recrystallized grain has minimal variations in orientation as shown by the absence of color variations/gradients. Further, recrystallization is known to span entire grains, and in FIG. 5B, the segmentation recovers the entire grains. This can be visually observed by comparing the grain boundaries of segmented regions of the map with corresponding grain boundaries of unsegmented regions of the map.

The recovery state of the metal alloy may be quantified, by the processor running computer readable code, by generating a scale of the recovery utilizing $\theta_{reference}$ and $\theta_{recovery}$ as two extremes of the scale. These angles may be assigned a label indicative of a recovery progression or a percentage of recovery. As one example, $\theta_{reference}$ may be labeled "no recovery" on the scale and $\theta_{recovery}$ that represents maximum possible recovery (as defined above) may be labeled "recovered" on the scale. As another example, $\theta_{reference}$ may be 0% recovery on the scale and $\theta_{recovery}$ that represents maximum possible recovery may be 100% recovery on the scale. In an example, the scale corresponding to the data in FIG. 3 may have $\theta_{reference}$ represent 0% recovery on the scale, falling at a peak local orientation deviation angle of about 1 degree, and $\theta_{recovery}$ represent 100% recovery on the scale, falling at a peak local orientation deviation angle of about 0.5 degrees. The scale would then be set for percent recovery falling within the 1 degree and 0.5 degree scale. If, for example, a peak local orientation deviation angle is measured to be about 0.75 degrees, then the percent recovery would be about 50% based on the scale.

Figure 6:
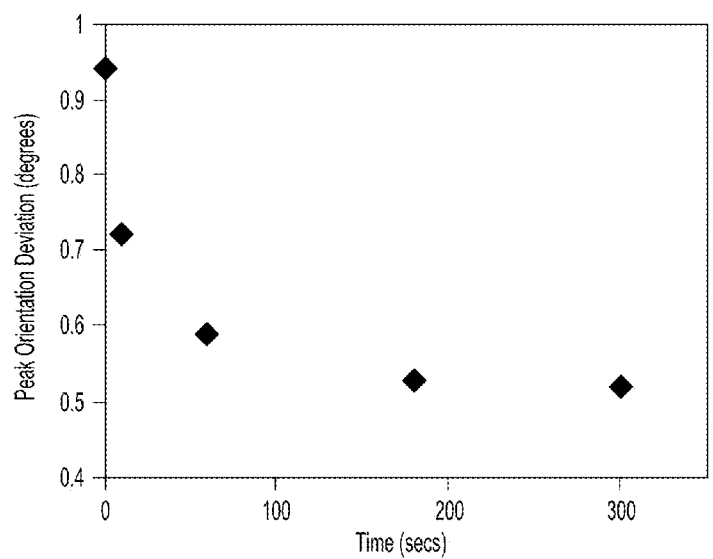
FIG. 6 is a plot showing the recovery kinetics of the AA5182 aluminum alloy sample, the kinetics being illustrated by the variation in peak local orientation deviation versus annealing time.

Once the recovery state of the metal alloy has been quantified, optimal heat treatment during metal forming may be identified for maximum utilization of recovery. This may be accomplished, for example, by generating kinetics data of the plastic strain recovery utilizing the peak orientation deviation data (e.g., the peak local orientation deviation angle). In an example, the kinetics data may be obtained by plotting the peak orientation deviation angle verses the annealing time, as shown in FIG. 6. As illustrated in FIG. 6, the peak orientation deviation angles corresponding to the mode of the distribution decrease exponentially with respect to the annealing time. A saturation point may be determined, which corresponds to the largest annealing time allowable beyond which very little useful recovery is possible. In other words, the saturation point is a point at which the metal alloy has recovered without recrystallization occurring. As such, the saturation point may be used to identify the end of useful recovery. From FIG. 6, the saturation point occurs at about 0.52 degrees, which corresponds to about 180 seconds of annealing time. For this sample then, a similar metal alloy could be annealed for about 180 seconds in order to limit recovery without recrystallization. It is believed that annealing temperature may be controlled utilizing the kinetics data. In an example, kinetics data may be used to determine optimal annealing temperature by constructing a curve similar to the one shown in FIG. 6. For this curve, the annealing time would remain constant, and the temperature may be varied. The plateau or saturation of the local orientation deviation values would indicate optimal annealing temperature for a given annealing time.

Another method of determining the recovery state of a metal alloy will now be described herein. This method may be used to determine the recovery state of a plastically-strained metal alloy; such as one that has been pre-formed by, e.g., a stamping operation or other similar pre-forming process. The method involves obtaining EBSD data of the metal alloy, and from the data, identifying a fluctuation in grain orientations of the metal alloy. The EBSD data may be obtained from the EBSD machine as previously described, and the fluctuation in grain orientations may be identified from the IPF maps and EBSD data.

By the processor of the EBSD machine, the local orientation deviation angle at each of a plurality of EBSD scan points is identified by comparing the fluctuation in grain orientations with a reference orientation at each scan point. Then an area fraction for the local orientation deviation angles of each of the scan points is plotted, and from the plot, determining that at least partial plastic strain recovery of the metal alloy has occurred. These method steps may be performed via the processes described previously for the other example method. For example, a comparison may be made between the curves on the plot. Partial recovery may be identified if the local orientation deviation angle at the peak of the corresponding curve is less than the local orientation deviation angle at the peak of the corresponding with the unrecovered metal alloy (i.e., the deformed metal alloy). A curve having two peaks indicates that recrystallization has started, and full recovery (without recrystallization) occurs just prior to the appearance of the second peak.

Although the example methods described above have been demonstrated utilizing the AA5182 aluminum alloy, it is to be understood that the methods may be performed for any metal alloy as previously mentioned. Further, it is believed that quantification of the plastic strain recovery of a metal alloy may be yet further developed, e.g., by understanding/studying the relationship between the grain orientation fluctuations and dislocation density that characterizes the recovery.

While several examples have been described in detail, it will be apparent to those skilled in the art that the disclosed examples may be modified. Therefore, the foregoing description is to be considered non-limiting.

The invention claimed is:

1. A method for determining a recovery state of a metal alloy, the method comprising:
   determining a fluctuation in a crystallographic grain orientation of the metal alloy, the determining being accomplished utilizing electron backscatter diffraction (EBSD) data of the metal alloy; and
   by a processor of an electron backscatter diffraction machine, utilizing a local orientation deviation quantifier to correlate the fluctuation in the crystallographic grain orientation of the metal alloy with a plastic strain recovery of the metal alloy, wherein the utilizing includes:
      evaluating, by the processor, a local average orientation deviation at each of a plurality of EBSD scan points of the metal alloy from a reference orientation at each of the plurality of EBSD scan points;
      plotting, by the processor, an area fraction of the local average orientation deviation at each of the plurality of EBSD scan points of the metal alloy, the EBSD scan points including a scan point for when the metal alloy is in a deformed state and an other scan point for when the metal alloy is in an at least partially recovered state;
      identifying, by the processor, $\theta_{reference}$, a local orientation deviation angle for the metal alloy in the deformed state, and $\theta_{recovery}$, a local orientation deviation angle for the metal alloy in the at least partially recovered state; and
      determining that at least partial recovery of the metal alloy has occurred when the $\theta_{recovery}$ is less than the $\theta_{reference}$.

2. The method as defined in claim 1 wherein the metal alloy is a precipitation-hardenable metal alloy.

3. The method as defined in claim 2 wherein the metal alloy is chosen from a precipitation-hardenable aluminum alloy, a precipitation-hardenable copper alloy, and a precipitation-hardenable magnesium alloy.

4. The method as defined in claim 1, further comprising quantifying, by the processor, the recovery state of the metal alloy by generating a scale of the recovery utilizing the $\theta_{recovery}$ and the $\theta_{reference}$.

5. The method as defined in claim 1 wherein the plotting of the area fraction of the local average orientation deviation produces a curve including:
   a single peak for $\theta_{recrystallization}$, a local orientation deviation angle signifying a recrystallization of the metal alloy;
   an other single peak for the $\theta_{recovery}$, wherein $\theta_{recovery}$ is greater than $\theta_{recrystallization}$; and
   two peaks, wherein one of the two peaks represents a local orientation deviation angle for partial recovery of the metal alloy, and an other of the two peaks represents a local orientation deviation angle for partial recrystallization.

6. The method as defined in claim 5, further comprising:
   quantifying, by the processor, the recovery state of the metal alloy by generating a scale of the recovery utilizing $\theta_{reference}$ as 0% recovery and $\theta_{recovery}$ as 100% recovery.

7. The method as defined in claim 1 wherein the evaluating of the local average orientation deviation is accomplished by calculating, by the processor, a difference between a measured orientation and the reference orientation, the reference orientation being a mean kernel orientation, a mean grain orientation, or a grain orientation at a user-specified point inside a grain.

8. The method as defined in claim 1, further comprising generating kinetics data of the plastic strain recovery of the metal alloy utilizing peak orientation deviation data.

9. The method as defined in claim 1 wherein the metal alloy is an automotive part formed by an automotive part forming process.

10. A method for determining a recovery state of a plastically-strained metal alloy, the method comprising:
    obtaining electron backscatter diffraction (EBSD) data of the metal alloy;
    from the EBSD data, identifying a fluctuation in grain orientations of the metal alloy;
    identifying, by a processor of an electron backscatter diffraction machine that generates the EBSD data, a local orientation deviation angle at each of a plurality of scan points in the EBSD by comparing the fluctuation in grain orientations with a reference orientation at each of the plurality of scan points in the EBSD data;
    plotting, by the processor, an area fraction for the local orientation deviation angles of each of the plurality of EBSD scan points; and
    from the plot, determining that at least partial plastic strain recovery of the metal alloy has occurred.

11. The method as defined in claim 10 wherein the metal alloy is a precipitation-hardenable metal alloy.

12. The method as defined in claim 10 wherein the identifying of the local orientation deviation angles is accomplished by calculating, by the processor, a difference between a measured orientation and the reference orientation, the reference orientation being a mean kernel orientation, a mean grain orientation, or a grain orientation at a user-specified point inside a grain.

13. The method as defined in claim 10 wherein the determining includes:
    correlating, by the processor, the fluctuation in the crystallographic grain orientations of the metal alloy by comparing the fluctuation of the at least partially recovered metal alloy with a fluctuation in crystallographic grain orientations of any of the metal alloy at an unrecovered state or the metal alloy in a fully recovered state.

14. The method as defined in claim 10 wherein the electron backscatter diffraction (EBSD) data of the metal alloy is obtained at predetermined times after the metal alloy is subjected to a thermo-mechanical treatment step.

15. The method as defined in claim 14 wherein the thermo-mechanical treatment step involves an annealing step.

16. A method of controlling a metal forming process, comprising:
    determining a recovery state of a metal alloy by the method of claim 1; and
    based on the recovery state of the metal alloy, determining operating parameters of a thermo-mechanical treatment step of the metal forming process.

* * * * *